United States Patent
Neya et al.

(10) Patent No.: US 11,332,621 B1
(45) Date of Patent: May 17, 2022

(54) ZINC OXIDE POWDER, DISPERSION, PAINT, AND COSMETIC

(71) Applicant: SUMITOMO OSAKA CEMENT CO., LTD., Tokyo (JP)

(72) Inventors: Tadashi Neya, Tokyo (JP); Masahiro Nobe, Tokyo (JP); Syunsuke Suma, Tokyo (JP)

(73) Assignee: SUMITOMO OSAKA CEMENT CO., LTD., Tokyo (JP)

( * ) Notice: Subject to any disclaimer, the term of this patent is extended or adjusted under 35 U.S.C. 154(b) by 0 days.

(21) Appl. No.: 17/393,245

(22) Filed: Aug. 3, 2021

(30) Foreign Application Priority Data

Nov. 30, 2020 (JP) .............................. JP2020-198905

(51) Int. Cl.
| | |
|---|---|
| *C09D 7/62* | (2018.01) |
| *C01G 9/02* | (2006.01) |
| *C09C 1/04* | (2006.01) |
| *C09D 17/00* | (2006.01) |
| *A61K 8/02* | (2006.01) |
| *A61K 8/58* | (2006.01) |
| *A61K 8/04* | (2006.01) |
| *A61Q 17/04* | (2006.01) |
| *C09C 3/12* | (2006.01) |
| *C08K 9/06* | (2006.01) |

(52) U.S. Cl.
CPC .............. *C09C 1/043* (2013.01); *A61K 8/022* (2013.01); *A61K 8/04* (2013.01); *A61K 8/585* (2013.01); *A61Q 17/04* (2013.01); *C09C 3/12* (2013.01); *C09D 7/62* (2018.01); *C09D 17/007* (2013.01); *A61K 2800/41* (2013.01); *A61K 2800/43* (2013.01); *C01P 2002/60* (2013.01); *C01P 2002/82* (2013.01); *C01P 2006/11* (2013.01); *C01P 2006/12* (2013.01); *C01P 2006/62* (2013.01); *C01P 2006/63* (2013.01); *C01P 2006/64* (2013.01); *C01P 2006/80* (2013.01); *C08K 9/06* (2013.01); *C08K 2201/006* (2013.01)

(58) Field of Classification Search
CPC .................................................. C09D 17/007
See application file for complete search history.

(56) References Cited

FOREIGN PATENT DOCUMENTS

JP        2013-001578 A        1/2013

*Primary Examiner* — Alexandre F Ferre
(74) *Attorney, Agent, or Firm* — Merchant & Gould P.C.

(57) ABSTRACT

A zinc oxide powder in which a BET specific surface area (X) of the powder is 1.5 m²/g or more and 65 m²/g or less, a value obtained by a formula: an apparent specific volume (mL/g) measured by a loose packing method of the zinc oxide powder/an apparent specific volume (mL/g) measured by a tapping method of the zinc oxide powder is 1.5 or more and 2.5 or less, and Formula (1) and Formula (2) shown below are satisfied.

$$A1/E2 = aX + 0.06 \quad (1)$$

$$(M2-M1)/E2 \geq 0.02 \quad (2)$$

10 Claims, No Drawings

ZINC OXIDE POWDER, DISPERSION, PAINT, AND COSMETIC

FIELD OF THE INVENTION

The present invention relates to a zinc oxide powder, a dispersion, a paint, and a cosmetic.

This application claims the benefit of Japanese Patent Application No. 2020-198905 filed on Nov. 30, 2020, the disclosure of which is herein incorporated by reference in its entire.

BACKGROUND OF THE INVENTION

Zinc oxide has an ultraviolet-shielding function, a gas transmission-suppressing function, and the like and is also highly transparent. Therefore, zinc oxide is used for applications requiring transparency such as ultraviolet-shielding films, ultraviolet-shielding glass, cosmetics, and gas barrier films.

Zinc oxide powders that are blended into paints or cosmetics are ordinarily required to have a high degree of whiteness. This is because zinc oxide powders having a low degree of whiteness cause coloration or affect the appearance of paints or cosmetics when blended into the paints or cosmetics.

For example, Patent Document 1 proposes zinc oxide having an ignition loss of 1.0% by mass or less and a degree of whiteness W of 95 or higher in order to suppress the coloration of zinc oxide.

PRIOR ART LITERATURE

Patent Documents

Patent Document 1: Japanese Unexamined Patent Application, First Publication No. 2013-001578

SUMMARY OF THE INVENTION

However, even a zinc oxide powder having a high degree of whiteness had a problem in that the zinc oxide powder turns yellow or the like and impairs the appearances of paints or cosmetics when energy is applied to blend the zinc oxide powder into the paints or the cosmetics. There has been a desire for realizing a control over the coloration of zinc oxide powders into yellow or the like.

The present invention has been made in consideration of the above-described circumstances, and an object of the present invention is to provide a zinc oxide powder coloration of which is suppressed even when energy is applied thereto, a dispersion, a paint, and a cosmetic that each contain the zinc oxide powder.

Means for Solving the Problems

That is, in a zinc oxide powder of a first aspect of the present invention, a BET specific surface area (X) of the powder is 1.5 m$^2$/g or more and 65 m$^2$/g or less, a value obtained by a formula: an apparent specific volume (mL/g) measured by a loose packing method of the zinc oxide powder/an apparent specific volume (mL/g) measured by a tapping method of the zinc oxide powder is 1.5 or more and 2.5 or less, and Formula (1) and Formula (2) shown below are satisfied.

$$A1/E2 = aX + 0.06 \quad (1)$$

$$(M2 - M1)/E2 \geq 0.02 \quad (2)$$

Here, X represents a specific surface area (unit: m$^2$/g) of the zinc oxide powder, A1 represents a spectrum value of a peak present in the vicinity of 580 cm$^{-1}$ in a Raman spectrum of the zinc oxide powder which is obtained by Raman spectroscopy, E2 represents a spectrum value of a peak present in the vicinity of 437 cm$^{-1}$ in the Raman spectrum, a represents a value of 0.001 or more and 0.025 or less, M2 represents a maximum value of the spectrum within a range of 1091 cm$^{-1}$ to 1170 cm$^{-1}$ of the Raman spectrum, and M1 represents a maximum value of the spectrum within a range of 1020 cm$^{-1}$ to 1090 cm$^{-1}$ of the Raman spectrum.

A dispersion of a second aspect of the present invention contains the zinc oxide powder of the present invention and a dispersion medium.

A paint of a third aspect of the present invention contains the zinc oxide powder of the present invention, a resin, and a dispersion medium.

A cosmetic of a fourth aspect of the present invention contains at least one selected from the group consisting of the zinc oxide powder of the present invention and the dispersion of the present invention.

Effects of the Invention

According to the zinc oxide powder of the present invention, since the BET specific surface area (X) of the powder is 1.5 m$^2$/g or more and 65 m$^2$/g or less, the value obtained by the formula: the apparent specific volume (mL/g) measured by the loose packing method of the zinc oxide powder/the apparent specific volume (mL/g) measured by the tapping method of the zinc oxide powder is 1.5 or more and 2.5 or less, and Formula (1) and Formula (2) are satisfied, it is possible to provide a zinc oxide powder coloration of which is suppressed even when energy is applied thereto.

According to the dispersion of the present invention, since the zinc oxide powder of the present invention is contained, coloration is suppressed even when the zinc oxide powder is dispersed with a high energy, and it is possible to obtain a dispersion which is highly transparent and coloration of which is suppressed.

According to the paint of the present invention, since the zinc oxide powder of the present invention is contained, it is possible to obtain a paint which is highly transparent and coloration of which is suppressed.

According to the cosmetic of the present invention, since at least one selected from the group consisting of the zinc oxide powder of the present invention and the dispersion of the present invention is contained, it is possible to obtain a cosmetic which is highly transparent and coloration of which is suppressed.

DETAILED DESCRIPTION OF THE INVENTION

An embodiment that is a preferred example of a zinc oxide powder, a dispersion, a paint, and a cosmetic of the present invention will be described. The present embodiment is simply a specific description for better understanding of the gist of the present invention and does not limit the present invention unless particularly specified. Omission, addition, substitution, and other modifications are possible within the scope of the gist of the present invention.

Zinc Oxide Powder

In a zinc oxide powder of the present embodiment, the BET specific surface area (X) of the powder is 1.5 m$^2$/g or more and 65 m$^2$/g or less, a value obtained by a formula: the apparent specific volume (mL/g) measured by a loose packing method of the zinc oxide powder/the apparent specific volume (mL/g) measured by a tapping method of the zinc oxide powder is 1.5 or more and 2.5 or less, and Formula (1) and Formula (2) shown below are satisfied.

$$A1/E2 = aX + 0.06 \quad (1)$$

$$(M2 - M1)/E2 \geq 0.02 \quad (2)$$

Here, X represents the specific surface area (unit: $m^2/g$) of the zinc oxide powder, A1 represents the spectrum value of a peak present in the vicinity of 580 $cm^{-1}$ in a Raman spectrum of the zinc oxide powder which is obtained by Raman spectroscopy, E2 represents the spectrum value of a peak present in the vicinity of 437 $cm^{-1}$ in the Raman spectrum, a represents 0.001 or more and 0.025 or less, M2 represents the maximum value of the spectrum within a range of 1091 $cm^{-1}$ to 1170 $cm^{-1}$ of the Raman spectrum, and M1 represents the maximum value of the spectrum within a range of 1020 $cm^{-1}$ to 1090 $cm^{-1}$ of the Raman spectrum.

The spectrum value of a peak refers to the value of the apex of the peak (the maximum value of the peak). The vicinity of 580 $cm^{-1}$ may refer to a range of, for example, 560 to 600, preferably 570 to 590, and more preferably 572 to 588, and the vicinity of 437 $cm^{-1}$ may refer to a range of, for example, 427 to 447 and preferably 432 to 442.

In the present specification, the apparent specific volume measured by the loose packing method can also be differently referred to as the loosely packed volume. In addition, the apparent specific volume measured by the tapping method can also be differently referred to as the tapped volume.

The content of zinc oxide in the zinc oxide powder (particles) of the embodiment is preferably 99.5% by mass or more, more preferably 99.7% by mass or more, and still more preferably 100% by mass. The zinc oxide powder of the embodiment also preferably consists of zinc oxide particles. The content of zinc oxide in the zinc oxide powder of the present embodiment refers to a value measured by the following method. This measurement method is a measurement method according to "Determination of Zinc Oxide" described in the Japanese Standards of Quasi-drug Ingredients 2006 (Supplement to the Japanese standards of quasi-drug ingredients).

The zinc oxide powder is put into a muffle furnace and ignited at 500° C. until the mass becomes constant (a state where the mass does not change is formed). After that, the zinc oxide powder is naturally cooled to room temperature in a glass desiccator containing silica gel. The naturally cooled zinc oxide powder is accurately weighed to 1.5 g, water (50 mL) and dilute hydrochloric acid (20 mL) are added thereto, and the mixture is heated to dissolve the zinc oxide powder. In a case where an unwanted substance remains, three droplets of nitric acid are added to the solution to fully dissolve the unwanted substance. This solution is cooled to room temperature, and the total amount is adjusted to 250 mL by adding water. An acetic acid-ammonium acetate buffer solution having a pH adjusted to 5.0 (10 mL) is added to this solution (25 mL), and the pH is adjusted to 5 to 5.5 by adding diluted ammonia water. After that, the amount is adjusted to 250 mL by adding water, a xylenol orange reagent (0.5 mL) is added to the solution as an indicator, and the solution is titrated with a 0.05 mol/L disodium edetate solution until the solution turns yellow. Since 1 mL of the 0.05 mol/L disodium edetate solution is equivalent to 4.069 mg of zinc oxide, it is possible to determine the content of zinc oxide in the zinc oxide powder from the amount of the 0.05 mol/L disodium edetate solution required for the titration. In the present measurement method, in a case where a value of more than 100% by mass is calculated, the content of zinc oxide is regarded as 100% by mass.

Assumed Mechanism of Coloration Suppression

Here, an assumed mechanism by which coloration is suppressed even when energy is applied to the zinc oxide powder of the present embodiment will be described.

The present inventors and the like newly obtained the following knowledge by performing a variety of studies across a broad range in detail.

When a high energy is applied to an ordinary zinc oxide powder, which is an aggregate of nanometer-sized zinc oxide particles, the zinc oxide powder turns yellow or the like. This coloration is considered to depend on an oxygen defect in the zinc oxide powder. Nanometer-sized zinc oxide particles are likely to agglomerate. Therefore, in the production process of the zinc oxide powder, zinc oxide particles are likely to agglomerate, and as a result, an oxygen defect is likely to be generated in the zinc oxide powder. When a high energy is applied to the zinc oxide powder, the agglomeration of the zinc oxide particles is unraveled, and the oxygen defect that is present in the agglomeration of the zinc oxide powder is exposed on the surface. As a result, the zinc oxide powder turns yellow or the like due to the oxygen defect. Therefore, in order to suppress the coloration of the zinc oxide powder, there is a need to decrease oxygen defects on the outside and inside of the zinc oxide powder.

In order to decrease oxygen defects on the outside and inside of the zinc oxide powder, in the production process of the zinc oxide powder, a sufficient amount of oxygen is supplied, and the apparent specific volume measured by the loose packing method/the apparent specific volume measured by the tapping method is controlled to be within the above-described range, whereby the generation of an oxygen defect can be suppressed.

The amount of the oxygen defect in the zinc oxide powder can be evaluated by Raman spectroscopy. In Raman spectroscopy, the peak (E2) in the vicinity of 437 $cm^{-1}$ is a peak derived from a ZnO wurtzite-type hexagonal crystal. In addition, the peak (A1) in the vicinity of 580 $cm^{-1}$ is a peak derived from a crystal distortion such as an oxygen defect. Therefore, a decrease in A1/E2 means that the number of oxygen defects in the zinc oxide powder decreases.

The peak intensity of A1 is affected by the easiness in crystal distortion. The peak intensity of A1 is affected by the sizes of the zinc oxide particles, that is, the magnitude of the BET specific surface area of the zinc oxide powder. Ordinarily, as the BET specific surface area of the zinc oxide powder increases, the crystals of the zinc oxide particles are more likely to be distorted, thus, the peak derived from crystal distortion such as an oxygen defect becomes higher, and A1/E2 increases. Therefore, A1/E2 is preferably within a predetermined range in consideration of the BET specific surface area.

The present inventors and the like found that, in a zinc oxide powder that satisfies Formula (1), the number of oxygen defects that contribute to coloration is small, and it is possible to suppress the coloration of the zinc oxide powder at the time of being blended into cosmetics.

Furthermore, the present inventors and the like found that, in a zinc oxide powder that satisfies Formula (1) and Formula (2), coloration is suppressed even when the zinc oxide powder is dispersed with a high energy.

The peaks of M2 and M1, which are observed within a range of 1020 cm$^{-1}$ to 1170 cm$^{-1}$, are assumed to be peaks derived from an impurity that is contained in the zinc oxide powder, respectively. The impurity and zinc oxide are different substances.

In the zinc oxide powder, ordinarily, the spectrum maximum value of a peak that is shown within a range of 1091 cm$^{-1}$ to 1170 cm$^{-1}$ is higher than or approximately equal to the maximum value of the spectrum of a peak that is shown within a range of 1020 cm$^{-1}$ to 1090 cm$^{-1}$. However, the present inventors found that, although the mechanism is not clear, when the maximum value of a peak that is shown within a range of 1020 cm$^{-1}$ to 1090 cm$^{-1}$ is higher than the maximum value of the spectrum of a peak that is shown within a range of 1091 cm$^{-1}$ to 1170 cm$^{-1}$, and a value divided by the spectrum value of E2 is equal to or higher than a predetermined value, it is possible to suppress the coloration of the zinc oxide powder when a high energy is applied thereto.

In order to obtain a zinc oxide powder that satisfies Formula (2), there is a need to decrease the amount of transition metals belonging to Group V to Group XI in the fourth period of the periodic table of the elements in the zinc oxide powder, specifically, the content obtained by summing the amounts of the individual elements of vanadium, chromium, manganese, iron, cobalt, nickel, and copper. An example of a method for decreasing the amount of the transition metals is a method in which a raw material having a high purity is used, a raw material from which transition metals have been removed is used, or the incorporation of transition metals is prevented in the manufacturing process. When Formula (2) is satisfied, it is possible to prevent coloration derived from an impurity.

The amount of transition metals is preferably 0.5 ppm or more and 20 ppm or less, more preferably 0.5 ppm or more and 15 ppm or less, and still more preferably 1 ppm or more and 10 ppm or less.

The reason therefor is not clear; however, when the amount of transition metals is 0.5 ppm or more and 20 ppm or less, it is possible to obtain a cosmetic having a natural tone in the case of blending the zinc oxide powder into the cosmetic.

In the present invention, the content obtained by summing the amounts of individual elements belonging to Group V to Group XI in the fourth period of the periodic table of the elements refers to a value measured by inductively coupled plasma atomic emission spectroscopy.

When the zinc oxide powder satisfies Formula (1) and Formula (2), the coloration of the zinc oxide powder is suppressed even when the zinc oxide powder is dispersed with a high energy. The upper limit value of (M2−M1)/E2 is not particularly limited. In a case where the value of M2 is too high, the amount of an impurity in the powder is large, and there is a possibility that the impurity may affect the quality stability. Therefore, the upper limit value of (M2−M1)/E2 is preferably 1.0 or less, more preferably 0.50 or less, still more preferably 0.20 or less, and particularly preferably 0.10 or less. The value indicated by (M2−M1)/E2 may be, for example, 0.02 to 0.16, 0.03 to 0.14, 0.04 to 0.12, 0.05 to 0.10, 0.06 to 0.08, or the like as necessary.

In the zinc oxide powder of the present embodiment, the apparent specific volume measured by the loose packing method/the apparent specific volume measured by the tapping method is within the above-described range. Since the zinc oxide powder is manufactured so as to have such a characteristic, it is possible to decrease the amount of an oxygen defect that remains in the zinc oxide powder and to determine an appropriate amount of the oxygen defect and an impurity amount that need to be decreased in order to suppress coloration depending on the BET specific surface area of the zinc oxide powder.

That is, it is possible to control the zinc oxide powder so as to contain zinc oxide particles having an unpreferable structure or state as little as possible by controlling the apparent specific volume measured by the loose packing method/the apparent specific volume measured by the tapping method. In addition, as a result, it is possible to more preferably control the amount of an oxygen defect that remains in the zinc oxide powder.

The value of A1/E2, which indicates the amount of an oxygen defect, is preferably small. Since the amount of an oxygen defect is affected by the particle diameters, the specific surface area (X) is also included in Formula (1).

Method for Measuring Each Characteristic of Zinc Oxide Powder

The BET specific surface area in the zinc oxide powder of the present embodiment may refer to a value measured by the BET method using a specific surface area-measuring device, for example, as a specific example, a full automatic specific surface area analyzer (trade name: Macsorb HM Model-1201 manufactured by Mountech Co., Ltd.).

The apparent specific volume (mL/g) measured by the loose packing method in the zinc oxide powder of the present embodiment refers to a value measured in accordance with JIS K 5101-12-1 "Test methods for pigments—Part 12: Apparent density or apparent specific volume—Section 1: Loose packing method". For the apparent specific volume measured by the loose packing method, tapping is performed 50 times.

The apparent specific volume (mL/g) measured by the tapping method in the zinc oxide powder of the present embodiment can be measured using a bulk density-measuring device, for example, as a specific example, a closely packed bulk density-measuring device (trade name: TVP-1 type, manufactured by Tsutsui Scientific Instruments Co., Ltd.). A specific measurement method will be described.

The mass (A) of a 150 mL graduated cylinder (inner diameter: 31 mm, manufactured by Tsutsui Scientific Instruments Co., Ltd.) is measured with an electronic balance. Zinc oxide powder (100 mL or more) is placed on a sieve having a mesh diameter of 500 μm. Next, the zinc oxide powder is wiped with a brush, and the zinc oxide powder is sifted. The zinc oxide powder that has passed through the sieve (approximately 100 mL) is put into the 150 mL graduated cylinder. The mass (B) of this graduated cylinder is measured with the electronic balance. This graduated cylinder is fixed to the closely packed bulk density-measuring device. The graduated cylinder is covered with a black rubber stopper so as to prevent the powder from scattering during tapping. The volume (V) of the zinc oxide powder at the time of being tapped 50 times in the closely packed bulk density-measuring device is read from the graduated cylinder. Next, the apparent specific volume is calculated by V/(B−A). It is possible to set the tapping width to 20 mm and the tapping speed to 30 times/minute. As described above, the tapping method is a method in which a container containing powder is tapped a plurality of times to tamp the powder in the container and measurement is performed.

The crystallite diameter in the zinc oxide powder of the present embodiment refers to the Scherrer diameter calculated from the Scherrer equation using the full width at half maximum and diffraction angle (2θ) of a diffraction peak of a (101) plane in a powder X-ray diffraction pattern measured with an X-ray diffraction apparatus, for example, as a specific example, an X-ray diffraction apparatus (trade name: AERIS, manufactured by Malvern Panalytical Ltd.).

Regarding the measurement conditions for the X-ray diffraction of the powder using the above-described apparatus, CuKα radiation is used as the radiation source, the output is set to 40 kV and 15 mA. In addition, measurement data that are obtained by X-ray diffraction measurement can be analyzed using data processing software AERIS (manufactured by Malvern Panalytical Ltd.). The Scherrer diameter can be calculated as described above.

The Raman spectrum obtained by Raman spectroscopy in the zinc oxide powder of the present embodiment may refer to a value obtained using a Raman spectral apparatus, as a specific example, a Raman spectrometer (Model No.: XploRAPLUS, manufactured by Horiba, Ltd.). As the measurement conditions in the case of using the above-described apparatus, for example, the object lens may be 10 times, the laser wavelength may be 532 nm, the grating may be 1200 nm, the slit may be 100 µm, the confocal hole may be 300 µm, the neutral density filter may be 10%, the spectroscope may be 1671.63, the measurement wavelength region may be 300 $cm^{-1}$ to 2000 $cm^{-1}$, the exposure time may be 10 seconds, the cumulated number may be twice, and the like.

In order to confirm the degree of coloration, the color difference may be measured when the zinc oxide powder of the present embodiment is cracked until D98 becomes 500 µm or less. For example, L*, a*, b* may be measured with a color difference meter, specifically, a spectroscopic color difference meter after the zinc oxide powder is cracked under a predetermined condition, for example, by 16000 rotations in a hammer mill. The difference of W* before and after the cracking (ΔW*) may also be obtained by computing $W^* = 100 - ((100-L^*)^2 + (a^*)^2 + (b^*)^2)^{1/2}$ (3) for the zinc oxide powder before and after the cracking. The value of ΔW* is selected depending on the conditions and may be, for example, 0.1 to 1.2, 0.2 to 1.0, or 0.3 to 0.8.

BET Specific Surface Area

The BET specific surface area in the zinc oxide powder of the present embodiment is 1.5 $m^2/g$ or more and 65 $m^2/g$ or less, preferably 2.0 $m^2/g$ or more and 60 $m^2/g$ or less, more preferably 2.5 $m^2/g$ or more and 50 $m^2/g$ or less, and still more preferably 3.0 $m^2/g$ or more and 45 $m^2/g$ or less.

When the BET specific surface area of the zinc oxide powder is adjusted to the above-described range, it is possible to enhance the transparency of dispersions, paints, cosmetics, and the like that contain this zinc oxide powder.

When the BET specific surface area is less than 1.5 $m^2/g$, the transparency of dispersions tends to deteriorate in a case where the zinc oxide powder is contained in a high concentration, which is not preferable. On the other hand, when the BET specific surface area exceeds 65 $m^2/g$, in a case where the zinc oxide powder is contained in a high concentration, the viscosity of dispersions is likely to increase, and there is a tendency that it becomes difficult to obtain uniform and highly fluid dispersions, which is not preferable.

The method for adjusting the BET specific surface area of the zinc oxide powder to the above-described range is not particularly limited, and an exemplary example is a method in which the average primary particle size converted from the BET specific surface area (BET-converted particle diameter) is adjusted to 15 nm or more and 715 nm or less. Ordinarily, as the primary particle size becomes larger, the specific surface area becomes smaller, and, as the primary particle size becomes smaller, the specific surface area becomes larger.

In addition, the BET specific surface area of the zinc oxide powder can be adjusted by adjusting the particle shapes or by providing micropores to the particles.

The zinc oxide powder of the present embodiment is, usually, formed of secondary particles, but may contain primary particles. In a case where the zinc oxide powder contains primary particles, the fractions of zinc oxide secondary particles and zinc oxide primary particles in the zinc oxide powder can be arbitrarily selected. For example, the fraction of the secondary particles may be 70% by mass or more, 80% by mass or more, 90% by mass or more, 95% by mass or more, 98% by mass or more, or 100% by mass.

Apparent Specific Volume Measured by Loose Packing Method

The apparent specific volume measured by the loose packing method in the zinc oxide powder of the present embodiment is preferably 1.0 mL/g or more and 7.5 mL/g or less, more preferably 3.0 mL/g or more and 7.5 mL/g or less, still more preferably 4.0 mL/g or more and 7.5 mL/g or less, and particularly preferably 5.0 mL/g or more and 7.5 mL/g or less.

When the apparent specific volume measured by the loose packing method of the zinc oxide powder is adjusted to the above-described range, it is possible to suppress a temporal increase in the viscosity of dispersions at the time of mixing the zinc oxide powder into a dispersion medium.

When the apparent specific volume measured by the loose packing method is 1.0 mL/g or more, the transparency of dispersions containing the zinc oxide powder improves, which is preferable. On the other hand, when the apparent specific volume measured by the loose packing method is 7.5 mL/g or less, it is possible to suppress a temporal increase in the viscosity of dispersions containing the zinc oxide powder, which is preferable.

The method for controlling the apparent specific volume measured by the loose packing method of the zinc oxide powder to be within the above-described range is not particularly limited. For example, in the case of producing the zinc oxide powder using a thermal decomposition method as described in Japanese Laid-open Patent Publication No. 60-255620, it is possible to control the apparent specific volume measured by the loose packing method of the zinc oxide powder to be within the above-described range by adjusting the apparent specific volume measured by the loose packing method of zinc oxalate, zinc hydroxide, zinc carbonate, basic zinc carbonate, or the like, which is a raw material, or by adjusting the thermal decomposition temperature.

For example, in the case of producing zinc oxide using a gas phase method as described in Japanese Laid-open Patent Publication No. 63-288914, it is possible to control the apparent specific volume measured by the loose packing method of the zinc oxide powder to be within the above-described range by appropriately adjusting temperatures in the production process.

Apparent Specific Volume Measured by Loose Packing Method/Apparent Specific Volume Measured by Tapping Method In the zinc oxide powder of the present embodiment, a value obtained by dividing the apparent specific volume (mL/g) measured by the loose packing method by the apparent specific volume (mL/g) measured by the tapping method (the apparent specific volume measured by the loose packing method/the apparent specific volume measured by the tapping method) is 1.5 or more and 2.5 or less. "The apparent specific volume measured by the loose packing method/the apparent specific volume measured by the tapping method" is preferably 1.55 or more and 2.30 or less, more preferably 1.60 or more and 2.00 or less, and still more preferably 1.70 or more and 2.00 or less.

When "the apparent specific volume measured by the loose packing method/the apparent specific volume measured by the tapping method" is 1.5 or more and 2.5 or less, it is possible to suppress a temporal increase in the viscosity of dispersions containing the zinc oxide powder. In a case where "the apparent specific volume measured by the loose packing method/the apparent specific volume measured by the tapping method" is outside the above-described range, it is difficult to suppress a temporal increase in the viscosity.

The mechanism that makes it possible to suppress a temporal increase in the viscosity of dispersions containing the zinc oxide powder with "the apparent specific volume measured by the loose packing method/the apparent specific volume measured by the tapping method" within the above-described range is not clear, but is assumed as follows.

The apparent specific volume measured by the loose packing method is a value of the volume of the powder per unit mass measured in a state where an air is contained among the particles of the powder. In contrast, the apparent specific volume measured by the tapping method is a value of the volume of the powder per unit mass measured in a state where some of the air among the particles of the powder has been removed by tapping. Therefore, the apparent specific volume measured by the loose packing method of the powder is usually larger than the apparent specific volume measured by the tapping method. In addition, ordinarily, as the particles of the powder become smaller, the amount of the air among the particles becomes larger, and the apparent specific volume measured by the loose packing method becomes larger.

However, in a case where the zinc oxide particles that configure the zinc oxide powder are coarse, since it is difficult to contain an air among the particles even during the measurement of the apparent specific volume measured by the loose packing method, the value of the apparent specific volume measured by the loose packing method becomes small, and the value of "the apparent specific volume measured by the loose packing method/the apparent specific volume measured by the tapping method" becomes close to one. In this case, since the agglomerated particle diameters of the zinc oxide powder are large, the zinc oxide powder becomes poor in transparency.

In addition, in a case where there are a number of pores in the zinc oxide particles or a case where a steric barrier in which a branched structure or the like attributed to fusion between the zinc oxide particles is significantly formed is generated, the air among the particles is not removed even in a method for measuring the apparent specific volume measured by the tapping method, the value of the apparent specific volume measured by the tapping method becomes large, and the value of "the apparent specific volume measured by the loose packing method/the apparent specific volume measured by the tapping method" becomes close to one. In this case, at the time of dispersing the zinc oxide powder or a surface-treated zinc oxide powder in a solvent, the structure of the zinc oxide particles collapses, the active surfaces of the zinc oxide particles are exposed, and the viscosity of dispersions increases.

Therefore, in order to increase the transparency and suppress an increase in the viscosity of dispersions, "the apparent specific volume measured by the loose packing method/the apparent specific volume measured by the tapping method" needs to be 1.5 or more.

On the other hand, "the apparent specific volume measured by the loose packing method/the apparent specific volume measured by the tapping method" exceeding 2.5 means that fine zinc oxide particles are included among the zinc oxide particles that configure the zinc oxide powder. When incorporated into the zinc oxide powder, zinc oxide particles having extremely fine particle diameters act as a cause of re-agglomeration of the zinc oxide particles in dispersions even after being dispersed in the solvent. Therefore, due to such a temporal change, the viscosity of the dispersions increases, and the transparency of the dispersions also deteriorates. Therefore, "the apparent specific volume measured by the loose packing method/the apparent specific volume measured by the tapping method" needs to be 2.5 or less.

The transparency and dispersion stability of dispersions are maintained by appropriately adjusting the structure and sizes of the zinc oxide particles. That is, "the apparent specific volume measured by the loose packing method/the apparent specific volume measured by the tapping method" in the zinc oxide powder of the present embodiment is an excellent parameter enabling the macroscopic understanding of the microscopic behaviors of each zinc oxide particle.

Therefore, it is possible to obtain dispersions in which a temporal increase in the viscosity is suppressed and the dispersion stability is excellent by measuring "the apparent specific volume measured by the loose packing method/the apparent specific volume measured by the tapping method" and controlling the sizes of the zinc oxide particles that configure the zinc oxide powder or the structure of the zinc oxide particles such that the apparent specific volume measured by the loose packing method/the apparent specific volume measured by the tapping method becomes 1.5 or more and 2.5 or less.

Crystallite Diameter

The crystallite diameter of the zinc oxide powder of the present embodiment is preferably 15 nm or more and 60 nm or less. The crystallite diameter may be 15 nm or more and 50 nm or less, 15 nm or more and 40 nm or less, 15 nm or more and 35 nm or less, 15 nm or more and 30 nm or less, 20 nm or more and 25 nm or less, or the like as necessary.

Crystallite Diameter (nm)/BET-Converted Particle Diameter (nm)

In the zinc oxide powder of the present embodiment, a value obtained by dividing the crystallite diameter (nm) by the BET-converted particle diameter (nm) obtained from the BET specific surface area is preferably 0.1 or more and 1.0 or less, more preferably 0.4 or more and 1.0 or less, still more preferably 0.5 or more and 1.0 or less, and far still more preferably 0.6 or more and 1.0 or less. The value may be 0.2 or more and 0.9 or less, 0.3 or more and 0.8 or less, or the like as necessary.

The zinc oxide powder having a BET specific surface area of 1.5 $m^2/g$ or more and 65 $m^2/g$ or less and a crystallite diameter of 15 nm or more and 60 nm or less has crystallinity favorable enough to obtain high transparency and a high ultraviolet-shielding property.

In order to improve the crystallinity of the zinc oxide powder, there is a need to increase, for example, temperatures in the production process of the zinc oxide powder to an extent that grains do not excessively grow.

(Method for Manufacturing Zinc Oxide Powder and Method for Adjusting Apparent Specific Volume)

A method for manufacturing the zinc oxide powder of the present embodiment is not particularly limited. For example, as the method for manufacturing the zinc oxide powder, there is a method in which, as described in Japanese Laid-open Patent Publication No. S60-255620, zinc oxalate, zinc hydroxide, zinc carbonate, basic zinc carbonate, or the like, which serves as a raw material, is produced by a thermal decomposition method. In addition, for example, there is a method in which zinc oxide powder is produced by a gas phase method in which metallic zinc vapor is oxidatively combusted as described in Japanese Laid-open Patent Publication No. S63-288014.

In order to produce the zinc oxide powder of the present embodiment, a method in which a material that increases the apparent specific volume measured by the loose packing method is added or an apparatus capable of increasing the apparent specific volume measured by the loose packing method is used at the time of producing the zinc oxide powder, a method in which the zinc oxide powder is produced under the supply of an excessive amount of oxygen, or the like is exemplified. In a zinc oxide powder having a large apparent specific volume measured by the loose packing method, since the agglomeration of the particles is suppressed, it is possible to reduce an oxygen defect in the zinc oxide powder. Regarding the control over the apparent specific volume measured by the loose packing method of the powder, a desired value can be obtained by combining a method described below, a method that has been used in the related art, and the like. Here, an excellent effect that can be obtained by controlling the apparent specific volume of the powder to be within a predetermined range has not yet been known and predicted.

In order to increase the apparent specific volume measured by the loose packing method of the zinc oxide powder, in the case of using a thermal decomposition method, for example, a method in which a foaming agent is mixed into a raw material for producing the zinc oxide powder in a small amount that is arbitrarily selected, for example, approximately 1% by mass is exemplified. As the foaming agent, it is possible to preferably use, for example, an inorganic foaming agent such as ammonium carbonate, ammonium hydrogen carbonate, ammonium nitrite, sodium boron hydride, calcium azide, sodium bicarbonate, ammonium bicarbonate, ammonium carbonate, ammonium nitrite, neutral magnesium carbonate, ferrous oxalate, ammonium persulfate, or sodium boron hydride or an organic foaming agent such as an azo compound such as azobisisobutyronitrile, a hydrazine compound such as diphenylsulfone-3,3'-disulfohydrazine, a semicarbazide compound, a triazole compound, or an N-nitroso compound.

Examples of an example of an apparatus for increasing the apparent specific volume measured by the loose packing method of the zinc oxide powder include a fluidized-bed calcinating furnace and the like capable of calcinating while feeding an air.

The apparent specific volume measured by the loose packing method and "the apparent specific volume measured by the loose packing method/the apparent specific volume measured by the tapping method" can be adjusted to desired ranges by adjusting the amount of the foaming agent or the calcinating temperature.

Examples of the method for manufacturing the zinc oxide powder of the present embodiment include a method in which ammonium carbonate (1% by mass), which is a foaming agent, is added to zinc carbonate having an apparent specific volume measured by the loose packing method of 1.0 mL/g to 7.5 mL/g and thermally decomposed at 300° C. to 700° C., preferably, 400° C. to 600° C. in a fluidized-bed calcinating furnace.

Surface-Treated Zinc Oxide Powder

For the zinc oxide powder of the present embodiment, a surface treatment may be performed on at least some of the surface of the zinc oxide powder with at least one of an inorganic component and an organic component. The zinc oxide powder on which the surface treatment has been performed with at least one of an inorganic component and an organic component as described above will be referred to as surface-treated zinc oxide powder.

The inorganic component and the organic component are appropriately selected depending on the applications of the zinc oxide powder.

In a case where the surface-treated zinc oxide powder of the present embodiment is used for cosmetics, the inorganic component and the organic component are not particularly limited as long as the inorganic component and the organic component are a surface treatment agent that is ordinarily used for cosmetics.

Examples of an example of the inorganic component include silica, alumina, and the like.

Examples of an example of the organic component include at least one component selected from the group consisting of a silane compound, a silicone compound, a fatty acid, a fatty acid soap, a fatty acid ester, and an organic titanate compound.

In addition, as the inorganic component or the organic component, a surfactant may be used.

In a case where the zinc oxide powder is surface-treated with at least one of the inorganic component and the organic component described above, it is possible to suppress the surface activity of the zinc oxide powder or to improve the dispersibility of the zinc oxide powder in dispersion media.

Examples of the silane compound that is used for the surface treatment include alkylsilane, fluoroalkylsilane, and the like.

Examples of the alkylsilane include methyltrimethoxysilane, ethyltrimethoxysilane, hexyltrimethoxysilane, octyltrimethoxysilane, octyltriethoxysilane, and the like.

Examples of the fluoroalkylsilane include trifluoromethylethyltrimethoxysilane, heptadecafluorodecyltrimethoxysilane, and the like.

Among these silane compounds, the alkylsilane is preferred, and octyltriethoxysilane is particularly preferred.

These silane compounds may be used singly or two or more silane compounds may be used in combination.

Examples of the silicone compound that is used for the surface treatment include silicone oil, methicone, dimethicone, hydrogen dimethicone, triethoxysilylethyl polydimethylsiloxyethyl dimethicone, triethoxysilylethyl polydimethylsiloxyethylhexyl dimethicone, (acrylate/tridecyl acrylate/triethoxysilylpropyl methacrylate/dimethicone methacrylate) copolymers, triethoxycaprylylsilane, and the like.

Examples of the silicone oil include methyl hydrogen polysiloxane, dimethyl polysiloxane, methylphenyl polysiloxane, and the like.

These silicone compounds may be used singly or two or more silicone compounds may be used in combination. In addition, as the silicone compound, a copolymer of these silicone compounds may also be used.

Examples of the fatty acid include palmitic acid, isooctadecanoic acid, stearic acid, lauric acid, myristic acid, behenic acid, oleic acid, rosin acid, 12-hydroxystearic acid, and the like.

Examples of the fatty acid soap include aluminum stearate, calcium stearate, aluminum 12-hydroxystearate, and the like.

Examples of the fatty acid ester include dextrin fatty acid esters, cholesterol fatty acid esters, sucrose fatty acid esters, starch fatty acid esters, and the like.

Examples of the organic titanate compound include isopropyl triisostearoyl titanate, isopropyl dimethacryl isostearoyl titanate, isopropyl tri(dodecyl) benzene sulfonyl titanate, neopentyl (diallyl)oxy tri(dioctyl) phosphate titanate, neopentyl (diallyl)oxy trineododecanoyl titanate, and the like.

In a case where the surface-treated zinc oxide powder of the present embodiment is used for industrial applications of ultraviolet-shielding films, gas barrier films, or the like, in addition to the inorganic component or the organic component that is used for cosmetics, an ordinary dispersant that is used to disperse particles such as an anionic dispersant, a cationic dispersant, a nonionic dispersant, a silane coupling agent, or a wetting dispersant can also be appropriately selected and used as the surface treatment agent.

In a case where the above-described surface treatment is performed, it is possible to suppress the surface activity of the zinc oxide powder or to improve the dispersibility of the zinc oxide powder in dispersion media.

In the surface-treated zinc oxide powder of the present embodiment, a value (D98 (μm)/BET-converted particle diameter (nm)) obtained by dividing the dry particle diameter D98 (μm) of the surface-treated zinc oxide powder by the BET-converted particle diameter (nm) of the surface-treated zinc oxide powder is preferably 0.01 or more and 5.0 or less, more preferably 0.01 or more and 4.5 or less, still more preferably 0.01 or more and 4.0 or less, and particularly preferably 0.01 or more and 3.0 or less. The value may be 0.01 or more and 1.0 or less, 0.15 or more and 0.80 or less, or 0.20 or more and 0.60 or less as necessary. The BET-converted particle diameter of the surface-treated zinc oxide powder can be calculated by applying the BET specific surface area of the surface-treated zinc oxide powder to Formula (5) shown below.

$$\text{BET-converted particle diameter (nm)} = 6000/(\text{BET specific surface area (m}^2\text{/g)} \times \rho \text{ (g/cm}^3)) \quad (5)$$

In Formula (5), ρ is the density of zinc oxide, and, in the specification of the present embodiment, ρ of 5.61 g/cm$^3$ is used.

The BET-converted particle diameter (nm) of the zinc oxide powder can be arbitrarily selected. For example, the diameter may be 15 to 715 nm or 15 to 550 nm. The diameter may be 15 to 250 nm, 15 to 200 nm, 20 to 100 nm, 20 to 50 nm, 25 to 40 nm, 30 to 35 nm, or the like as necessary. When the "D98/BET-converted particle diameter" of the surface-treated zinc oxide powder is within the above-described range, it is possible to suppress the texture of rough surface of the surface-treated zinc oxide powder.

The dry particle diameter D98 refers to the value of the particle diameter at a cumulative volume percentage of 98% in the case of measuring the volume particle size distribution of the zinc oxide powder in a dry manner using a laser diffraction-type particle size distribution-measuring device (Model No.: Mastersizer 3000, manufactured by Malvern Panalytical Ltd.).

The method for manufacturing the surface-treated zinc oxide powder of the present embodiment is not particularly limited, and a well-known method may be appropriately performed depending on a component that is used for the surface treatment.

In addition, the zinc oxide powder that has undergone the surface treatment may be subjected to a cracking treatment.

The amount of zinc oxide contained in the surface-treated zinc oxide powder of the present embodiment is preferably 80% to 99% by mass and more preferably 82% to 97% by mass.

Examples of an example of a method for the surface treatment include the following method.

The zinc oxide powder of the present invention that is not surface-treated, at least one of the inorganic component and the organic component that is used for the surface treatment, and, as necessary, one or more arbitrarily-selected solvents such as pure water or isopropyl alcohol are mixed together by an arbitrarily-selected method or apparatus. Preferred examples of the solvents include aqueous solvents and the like. The total amount of the inorganic component and/or the organic component that are mixed may be, for example, 1 to 25 parts by mass and is preferably 3 to 22 parts by mass with respect to 100 parts by mass of the zinc oxide particles. The amount of the solvents can be arbitrarily selected. After the mixing, the mixture obtained at an arbitrarily-selected temperature may be dried in order to remove at least one part of the solvent. The temperature for the drying can be arbitrarily selected and is, for example, 50° C. to 200° C. or the like, preferably 60° C. to 150° C., and more preferably 70° C. to 120° C. In addition, a heat treatment may be performed in order to further progress the surface treatment reaction. The temperature for the heat treatment can be arbitrarily selected and is, for example, 200° C. to 800° C. or the like, preferably 200° C. to 700° C., and more preferably 200° C. to 600° C. The obtained dried substance or heat-treated substance (surface-treated zinc oxide powder) may be cracked by an arbitrarily-selected method or apparatus under an arbitrarily-selected condition until, for example, D98 becomes 500 μm or less. The cracked substance may be further dried. The drying temperature can be arbitrarily selected and is, for example, 50° C. to 200° C. or the like, preferably 60° C. to 150° C., and more preferably 70° C. to 120° C. The surface-treated zinc oxide powder of the present embodiment may be controlled such that the value obtained by dividing the dry particle diameter D98 (μm) by the BET-converted particle diameter (nm) becomes 0.01 or more and 5 or less by controlling a manufacturing condition.

Dispersion

A dispersion of the present embodiment contains the zinc oxide powder of the present embodiment and a dispersion medium. Examples of the dispersion of the present embodiment include a paste-form dispersion having a high viscosity.

The content of the zinc oxide powder in the dispersion of the present embodiment is not particularly limited, can be arbitrarily selected, and is, for example, preferably 10% by mass or more and 90% by mass or less, more preferably 20% by mass or more and 85% by mass or less, and still more preferably 30% by mass or more and 80% by mass or less with respect to the total amount of the dispersion.

When the content of the zinc oxide powder in the dispersion is within the above-described range, a preferred characteristic of the zinc oxide powder can be obtained, and it is possible to suppress a temporal increase in the viscosity of the dispersion.

The dispersion medium is appropriately selected depending on the application of the dispersion. Examples of preferred dispersion media will be described below, but the dispersion medium in the present embodiment is not limited thereto. The following dispersion media may be used singly or dispersion media from the following examples may be used in combination.

As examples of an example of the dispersion medium, for example, water, an alcohol, an ester, an ether, and the like are preferably used.

Examples of the alcohol include methanol, ethanol, 1-propanol, 2-propanol, 1-butanol, 2-butanol, octanol, glycerin, and the like.

Examples of the ester include ethyl acetate, butyl acetate, ethyl lactate, propylene glycol monomethyl ether acetate, propylene glycol monoethyl ether acetate, γ-butyrolactone, and the like.

Examples of the ether include diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, diethylene glycol monoethyl ether, and the like.

These dispersion media may be used singly or two or more dispersion media may be used in a mixture form.

In addition, as examples of additional dispersion media, ketones, aromatic hydrocarbons, cyclic hydrocarbons, amides, and chain-like polysiloxanes are also preferably used.

Examples of the ketones include acetone, methyl ethyl ketone, methyl isobutyl ketone, acetyl acetone, cyclohexanone, and the like.

Examples of the aromatic hydrocarbons include benzene, toluene, xylene, ethyl benzene, and the like.

Examples of the cyclic hydrocarbons include cyclohexane and the like.

Examples of the amides include dimethylformamide, N,N-dimethylacetoacetamide, N-methylpyrrolidone, and the like.

Examples of the chain-like polysiloxanes include dimethyl polysiloxane, methyl phenyl polysiloxane, diphenyl polysiloxane, and the like.

These dispersion media may be used singly or two or more dispersion media may be used in a mixture form.

In addition, as additional dispersion media, cyclic polysiloxanes and denatured polysiloxanes are also preferably used.

Examples of the cyclic polysiloxanes include octamethyl cyclotetrasiloxane, decamethylcyclopentasiloxane, dodecamethyl cyclohexasiloxane, and the like.

Examples of the denatured polysiloxanes include amino-denatured polysiloxane, polyether-denatured polysiloxane, alkyl-denatured polysiloxane, fluorine-denatured polysiloxane, and the like.

These dispersion media may be used singly or two or more dispersion media may be used in a mixture form.

In addition, as additional dispersion media, hydrophobic dispersion media such as hydrocarbon oils such as liquid paraffin, squalane, isoparaffin, branched chain-like light paraffin, petrolatum, and ceresin, ester oils such as isopropyl myristate, cetyl isooctanoate, and glyceryl trioctanoate, silicone oils such as decamethylcyclopentasiloxane, dimethyl polysiloxane, and methyl phenyl polysiloxane, higher fatty acids such as lauric acid, myristic acid, palmitic acid, and stearic acid, and higher alcohols such as lauryl alcohol, cetyl alcohol, stearyl alcohol, hexyl dodecanol, and isostearyl alcohol may be used.

The dispersion of the present embodiment may include an ordinarily-used additive as long as the characteristic thereof is not impaired. Examples of the additive include a dispersant, a stabilizer, a water-soluble binder, a viscosity improver, an oil-soluble preservative, an ultraviolet absorber, an oil-soluble chemical, an oil-soluble pigment, an oil-soluble protein, a plant oil, an animal oil, and the like. These additives may be contained in an arbitrarily selected amount.

The method for manufacturing the dispersion of the present embodiment is not particularly limited, and examples of the method include a method in which the zinc oxide powder of the present embodiment and a dispersion medium are mechanically dispersed using a well-known dispersion apparatus.

Examples of the dispersion apparatus include a stirrer, a planetary mixer, a homogenizer, an ultrasonic homogenizer, a sand mill, a ball mill, a roll mill, and the like.

The dispersion of the present embodiment can be preferably used for, in addition to cosmetics, paints and the like having an ultraviolet-shielding function, a gas transmission-suppressing function, or the like.

Paint

A paint of the present embodiment contains the zinc oxide powder of the present embodiment, a resin, and a dispersion medium.

The content of the zinc oxide powder in the paint of the present embodiment may be appropriately adjusted in accordance with a desired characteristic. The content of the zinc oxide powder in the paint of the present embodiment is, for example, preferably 10% by mass or more and 40% by mass or less, more preferably 15% by mass or more and 35% by mass or less, and still more preferably 20% by mass or more and 30% by mass or less with respect to the total amount of the paint.

When the content of the zinc oxide powder in the paint is within the above-described range, the characteristic of the zinc oxide powder can be obtained, and it is possible to suppress a temporal increase in the viscosity of the paint.

The dispersion medium is not particularly limited as long as the dispersion medium is ordinarily used for industrial applications, and examples thereof include water, an alcohol, and an organic solvent such as methyl acetate, ethyl acetate, toluene, methyl ethyl ketone, or methyl isobutyl ketone.

The content of the dispersion medium in the paint of the present embodiment is not particularly limited and is appropriately adjusted depending on the intended characteristic of the paint.

The resin can be used without any particular limitations as long as the resin is ordinarily used for industrial applications, and examples thereof include an acrylic resin, an epoxy resin, a urethane resin, a polyester resin, a silicone resin, and the like.

The content of the resin in the paint of the present embodiment is not particularly limited and is appropriately adjusted depending on the intended characteristic of the paint.

The paint of the present embodiment may include an ordinarily-used additive as long as the characteristic thereof is not impaired. Examples of the additives include a polymerization initiator, a dispersant, a preservative, and the like.

The method for manufacturing the paint of the present embodiment is not particularly limited, and examples of the method include a method in which the zinc oxide powder of the present embodiment, the resin, and the dispersion medium are mechanically mixed together using a well-known mixing apparatus. In addition, there is another method in which the above-described dispersion and the resin are mechanically mixed together using a well-known mixing apparatus.

Examples of the mixing apparatus include a stirrer, a planetary mixer, a homogenizer, an ultrasonic homogenizer, and the like.

A coated film can be formed by applying the paint of the present embodiment to a plastic base material such as a polyester film using an ordinary application method such as a roll coating method, a flow coating method, a spray coating method, a screen printing method, a brush coating method, or an immersion method. The coated film can be used as an ultraviolet-shielding film or a gas barrier film.

Cosmetic

A cosmetic of an embodiment of the present embodiment contains at least one selected from the group consisting of the zinc oxide powder of the present embodiment and the dispersion of the present embodiment. That is, the cosmetic may contain either or both of the zinc oxide powder and the dispersion.

A cosmetic of another embodiment contains a base and at least one selected from the group consisting of the zinc oxide powder of the present embodiment and the dispersion of the present embodiment, which is to be dispersed in the base. That is, the cosmetic may contain either or both of the zinc oxide powder and the dispersion and the base material.

The cosmetic of the present embodiment can be obtained by, for example, blending the dispersion of the present embodiment into a base such as an emulsion, a cream, a foundation, a lip stick, a blush, or an eye shadow as in the related art.

In addition, the cosmetic may also be obtained by blending the zinc oxide powder of the present embodiment into an oil phase or a water phase so as to produce an ON-type or W/O-type emulsion and then blending the emulsion with a base.

Hereinafter, a sunscreen cosmetic will be specifically described.

The content rate of the zinc oxide powder in the sunscreen cosmetic can be arbitrarily selected; however, in order to effectively shield ultraviolet rays, particularly, long-wavelength ultraviolet rays (UVA), the content rate of the zinc oxide powder is preferably 1% by mass or more and 30% by mass or less, more preferably 3% by mass or more and 20% by mass or less, and still more preferably 5% by mass or more and 15% by mass or less with respect to the total amount of the cosmetic.

The sunscreen cosmetic may include a hydrophobic dispersion medium, inorganic fine particles or an inorganic pigment other than the zinc oxide powder, a hydrophilic dispersion medium, oil and fat, a surfactant, a moisturizing agent, a viscosity improver, a pH adjuster, a nutritional supplement, an antioxidant, a perfume, and the like as necessary.

Examples of the hydrophobic dispersion medium include a hydrocarbon oil such as such as liquid paraffin, squalane, isoparaffin, branched chain-like light paraffin, petrolatum, or ceresin, an ester oil such as isopropyl myristate, cetyl isooctanoate, or glyceryl trioctanoate, a silicone oil such as decamethylcyclopentasiloxane, dimethyl polysiloxane, or methyl phenyl polysiloxane, a higher fatty acid such as lauric acid, myristic acid, palmitic acid, or stearic acid, and a higher alcohol such as lauryl alcohol, cetyl alcohol, stearyl alcohol, hexyl dodecanol, or isostearyl alcohol.

Examples of the inorganic fine particles or the inorganic pigment other than the zinc oxide powder include calcium carbonate, calcium phosphate (apatite), magnesium carbonate, calcium silicate, magnesium silicate, aluminum silicate, kaolin, talc, titanium oxide, aluminum oxide, yellow oxide of iron, γ-iron oxide, cobalt titanate, cobalt violet, silicon oxide, and the like.

The sunscreen cosmetic may further contain at least one organic ultraviolet absorber. The content of the organic ultraviolet absorber may be appropriately adjusted so as to obtain a desired ultraviolet-shielding property. For the organic ultraviolet absorber the amount of which that can be blended into sunscreen cosmetic is regulated, the upper limit may be appropriately adjusted according to the regulation of each country. For example, the content of the organic ultraviolet absorber may be 20% by mass or less, 15% by mass or less, 12% by mass or less, or 10% by mass or less, 9% by mass or less, 8% by mass or less, 6% by mass or less, 4% by mass or less, or 3% by mass or less.

Examples of the organic ultraviolet absorber include a benzotriazole-based ultraviolet absorber, a benzoyl methane-based ultraviolet absorber, a benzoic acid-based ultraviolet absorber, an anthranilic acid-based ultraviolet absorber, a salicylic acid-based ultraviolet absorber, a cinnamic acid-based ultraviolet absorber, a silicone-based ultraviolet absorber, a triazine-based ultraviolet absorber, an imidazole-based ultraviolet absorber, a camphor-based ultraviolet absorber, a benzophenone-based ultraviolet absorber, organic ultraviolet absorbers other than the above-described ultraviolet absorbers, and the like.

Examples of an example of the benzotriazole-based ultraviolet absorber include 2-(2'-hydroxy-5'-t-octylphenyl)benzotriazole, 2-(2'-hydroxy-5'-methylphenyl) benzotriazole, and the like.

Examples of the benzoyl methane-based ultraviolet absorber include dibenzalazine, dianisoylmethane, 4-tert-butyl-4'-methoxydibenzoylmethane, 1-(4'-isopropylphenyl)-3-phenyl propane-1,3-dione, 5-(3,3'-dimethyl-2-norbornylidene)-3-pentane-2-one, and the like.

Examples of an example of the benzoic acid-based ultraviolet absorber include para-aminobenzoic acid (PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA methyl ester, ethylhexyl dimethyl PABA, amyl dimethyl PABA, and the like.

Examples of the anthranilic acid-based ultraviolet absorber include homo menthyl-N-acetyl anthranilate and the like.

Examples of an example of the salicylic acid-based ultraviolet absorber include amyl salicylate, menthyl salicylate, homo menthyl salicylate, octyl salicylate, phenyl salicylate, benzyl salicylate, p-2-propnol phenyl salicylate, ethylhexyl salicylate, and the like.

Examples of an example of the cinnamic acid-based ultraviolet absorber include octyl methoxycinnamate, di-para methoxy cinnamate-mono-2-glyceryl ethylhexanoate, octyl cinnamate, ethyl-4-isopropyl cinnamate, diisoprpyle methyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate(2-ethylhexyl-p-methoxy cinnmate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-diparamethoxy cinnamate, ferulic acid, cinoxate, isophenyl trimethoxycinnamate trisiloxane, isopropyl methoxycinnamate, and the like.

Examples of an example of the silicone-based ultraviolet absorber include [3-bis(trimethylsiloxy)methylsilyl-1-methylpropyl]-3,4,5-trimethoxy cinnamate, [3-bis(trimethylsiloxy)methylsilyl-3-methylpropyl]-3,4,5-trimethoxy cinnamate, [3-bis(trimethylsiloxy)methylsilylpropyl]-3,4,5-trimethoxy cinnamate, [3-bis(trimethylsiloxy)methylsilylbutyl]-3,4,5-trimethoxy cinnamate, [3-tris(trimethylsiloxy)silylbutyl]-3,4,5-trimethoxy cinnamate, [3-tris(trimethylsiloxy)silyl-1-methylpropyl]-3,4-dimethoxy cinnamate, polysilicone-15, drometrizole trisiloxane, and the like.

Examples of an example of the triazine-based ultraviolet absorber include bis-ethylhexyloxyphenol methoxyphenyl triazine, ethylhexyl triazone, methylene bis-benzotriazolyl tetramethylbutylphenol, tris-biphenyl triazine, diethylhexyl butamido triazone, and the like.

Examples of an example of the imidazole-based ultraviolet absorber include disodium phenyl dibenzimidazole tetrasulfonate, phenylbenzimidazole sulfonic acid, ethylhexyl dimethoxybenzylidene dioxoimidazolidine propionate, and the like.

Examples of an example of the camphor-based ultraviolet absorber include 3-(4'-methylbenzylidene)-d,l-camphor, 3-benzylidene-d,l-camphor, terephthalylidene dicamphor sulfonic acid, camphor benzalkonium methsulfate, benzylidene camphor sulfonic acid, polyacrylamidomethyl benzylidene camphor, and the like.

Examples of an example of the benzophenone-based ultraviolet absorber include oxybenzone-1, oxybenzone-2, oxybenzone-3, oxybenzone-4, oxybenzone-5, oxybenzone-6, oxybenzone-7, oxybenzone-8, oxybenzone-9,4-(2-β-glucopyranosiloxy)propoxy-2-hydroxybenzophenone, and the like.

Examples of the organic ultraviolet absorbers other than the above-described ultraviolet absorbers include urocanic acid, ethylurocanate ester, 5-methyl-2-phenylbenzoxazole, 5-(3,3'-dimethyl-2-norbornylidene)-3-pentane-2-one, diethylamino hydroxybenzoyl hexyl benzoate, octocrylene, a silicone-denatured ultraviolet absorber, a fluorine-denatured ultraviolet absorber, and the like.

As described above, according to the zinc oxide powder of the present embodiment, since the BET specific surface area and the ratio of "the apparent specific volume measured by the loose packing method/the apparent specific volume measured by the tapping method" are within the above-described ranges and are adjusted so as to satisfy Formula (1) and Formula (2), it is possible to suppress the coloration of the zinc oxide powder even when the zinc oxide powder is dispersed with a high energy at the time of producing cosmetics.

In addition, the use of this zinc oxide powder makes it possible to obtain dispersions or cosmetics having high transparency and an excellent ultraviolet-shielding property.

The above-described characteristic is an extremely excellent effect.

According to the surface-treated zinc oxide powder of the present embodiment, the surface treatment is performed on at least some of the surface of the zinc oxide powder of the present embodiment with at least one of the inorganic component and the organic component. Therefore, it is possible to suppress the surface activity of the zinc oxide powder and to improve the dispersibility in dispersion media. In addition, it is possible to suppress the coloration of the zinc oxide powder even when the zinc oxide powder is dispersed with a high energy at the time of producing dispersions containing this surface-treated zinc oxide powder.

The dispersion of the present embodiment contains the zinc oxide powder or surface-treated zinc oxide powder of the present embodiment. Therefore, it is possible to mix the dispersion with a high energy at the time of blending the dispersion into cosmetics.

The paint of the present embodiment contains the zinc oxide powder or surface-treated zinc oxide powder of the present embodiment. Therefore, it is possible to suppress the coloration of the zinc oxide powder and to obtain paints having a natural tone.

The cosmetic of the present embodiment contains the zinc oxide powder or surface-treated zinc oxide powder of the present embodiment. Therefore, it is possible to suppress the coloration of the zinc oxide powder and to obtain cosmetics having a natural tone.

EXAMPLES

Hereinafter, the present invention will be more specifically described with examples and comparative examples, but the present invention is not limited to the following examples.

Raman Spectroscopy

Raman spectroscopy was measured using a Raman spectrometer (Model No.: XploRAPLUS, manufactured by Horiba, Ltd.) under the following conditions. The measurement results are shown in Table 1.

Object lens: 10 times
Laser wavelength: 532 nm
Grating: 1200 nm
Slit: 100 μm
Confocal hole: 300 μm
Neutral density filter: 10%
Spectroscope: 1671.63
Measurement wavelength region: 300 cm$^{-1}$ to 2000 cm$^{-1}$
Exposure time: 10 seconds
Cumulated number: Twice
Amount of transition metals The amount of transition metals was obtained by measuring the amounts of vanadium, chromium, manganese, iron, cobalt, nickel, and copper that were contained in a zinc oxide powder using an ICP emission spectrophotometer (Model No.: ICP-AES700-ES, manufactured by Varian Medical Systems, Inc.) and calculating the total thereof. When the total amount was 0.5 ppm or more and 20 ppm or less, the amount of transition metals was evaluated as "○ (permissible)", and, in a case where the total amount exceeded 20 ppm, the amount of transition metals was evaluated as "X (impermissible)". The measurement results are shown in Table 1.

Method for Manufacturing Zinc Oxide Powder

Example 1

A zinc oxide powder A1 (BET specific surface area: 39.8 m$^2$/g, apparent specific volume measured by loose packing method: 5.2 mL/g, apparent specific volume measured by tapping method: 2.9 mL/g, A1/E2 in Formula (1): 0.17, a in Formula (1): 0.003, (M2−M1)/E2 in Formula (2): 0.081, and crystallite diameter: 16 nm) was prepared. The above-described characteristic, crystallite diameter, BET-converted particle diameter, amount of transition metals, and the like of the zinc oxide powder A1 are shown in Table 1.

Next, in order to evaluate coloration, the zinc oxide powder A1 (500 g) was cracked by 16000 rotations in a hammer mill until D98 became 500 μm or less. That is, a high energy was applied to the zinc oxide powder A1.

L*, a*, b* of the zinc oxide powder A1 before and after the cracking were measured with a spectroscopic color difference meter (Model No. TC-1800, manufactured by Tokyo Denshoku. Co., Ltd.).

In addition, W* that is calculated from Formula (3) and indicates coloration was calculated to evaluate the coloration status of the zinc oxide powder before and after the cracking.

$$W^* = 100 - ((100-L^*)^2 + (a^*)^2 + (b^*)^2)^{1/2} \quad (3)$$

In addition, $\Delta W^*$ that is calculated from Formula (4) and indicate a color difference was calculated. An increase in $\Delta W^*$ indicates an increase in the color difference before and after the cracking.

$$\Delta W^* = W^* \text{before cracking} - W^* \text{after cracking} \quad (4)$$

In addition, the amounts of the transition metals that were contained in the zinc oxide powder before the cracking was measured and the total thereof was calculated. In addition, whether or not Formula (1) was satisfied was checked. The results are shown in Table 1.

Production of Surface-Treated Zinc Oxide Powder

A mixed liquid of octyltriethoxysilane (trade name: KBE-3083, manufactured by Shin-Etsu Chemical Co., Ltd.) (6 parts by mass), the zinc oxide powder A1 (100 parts by mass), pure water (0.6 parts by mass), and isopropyl alcohol (34.1 parts by mass) was mixed in a Henschel mixer.

Next, the mixed liquid was dried at 80° C. until the isopropyl alcohol was removed. Next, the obtained dried substance was dried at 120° C. for three hours, thereby obtaining a surface-treated zinc oxide powder B1 of Example 1.

Production of Dispersion

The surface-treated zinc oxide powder B1 of Example 1 (50 parts by mass), PEG-9 polydimethylsiloxyethyl dimethicone (trade name: KF-6028, manufactured by Shin-Etsu Chemical Co., Ltd.) (10 parts by mass), and decamethylcyclopentasiloxane (trade name: SH245Fluid, manufactured by Dow Toray Co., Ltd.) (40 parts by mass) were dispersed using a bead mill, thereby obtaining a dispersion C1 of Example 1.

Evaluation of Viscosity and Temporal Stability of Dispersion

The viscosity of the dispersion C1 of Example 1 was measured under the following conditions using a rheometer (trade name: Modular Compact Rheometer MCR 102, manufactured by Anton Paar GmbH). The results are shown in Table 1.

Measurement temperature: 25° C.
Jig: Cone plate CP25-2
Shear rate: 1/sec

This dispersion was stored at 50° C. for 28 days, and the viscosity was measured under the same conditions as described above. The results are shown in Table 1.

Evaluation of Transparency and Ultraviolet-Shielding Property

The dispersion of Example 1 was diluted with decamethylcyclopentasiloxane such that the content of the surface-treated zinc oxide powder became 0.005% by mass. The linear transmittances of this diluted solution at 308 nm and 555 nm were measured using an UV-visible/NIR spectrophotometer (Model No.: V-770, manufactured by JASCO Corporation). The results are shown in Table 1.

A low transmittance at 308 nm indicates that the ultraviolet-shielding property is favorable. Therefore, the linear transmittance at 308 nm is preferably low.

A high transmittance at 555 nm indicates that the transparency is favorable. Therefore, the transmittance at 555 nm is preferably high.

Example 2

Instead of the zinc oxide powder A1, a zinc oxide powder A2 (BET specific surface area: 29.6 m$^2$/g, apparent specific volume measured by loose packing method: 5.1 mL/g, apparent specific volume measured by tapping method: 2.7 mL/g, A1/E2 in Formula (1): 0.16, a in Formula (1): 0.004, (M2−M1)/E2 in Formula (2): 0.096, and crystallite diameter: 21 nm) was prepared. A surface-treated zinc oxide powder B2 of Example 2 and a dispersion C2 containing the surface-treated zinc oxide powder B2 were obtained in completely the same manner as in Example 1 except the use of the zinc oxide powder A2. The results of the same evaluations as in Example 1 are shown in Table 1.

Example 3

Instead of the zinc oxide powder A1, a zinc oxide powder A3 (BET specific surface area: 34.6 m$^2$/g, apparent specific volume measured by loose packing method: 6.4 mL/g, apparent specific volume measured by tapping method: 2.9 mL/g, A1/E2 in Formula (1): 0.12, a in Formula (1): 0.002, (M2−M1)/E2 in Formula (2): 0.093, and crystallite diameter: 18 nm) was prepared. A surface-treated zinc oxide powder B3 of Example 3 and a dispersion C3 containing the surface-treated zinc oxide powder B3 were obtained in completely the same manner as in Example 1 except the use of the zinc oxide powder A3. The results of the same evaluations as in Example 1 are shown in Table 1.

Example 4

Instead of the zinc oxide powder A1, a zinc oxide powder A4 (BET specific surface area: 36.5 m$^2$/g, apparent specific volume measured by loose packing method: 3.7 mL/g, apparent specific volume measured by tapping method: 2.2 mL/g, A1/E2 in Formula (1): 0.72, a in Formula (1): 0.018, (M2−M1)/E2 in Formula (2): 0.025, and crystallite diameter: 16 nm) was prepared. A surface-treated zinc oxide powder B4 of Example 4 and a dispersion C4 containing the surface-treated zinc oxide powder B4 were obtained in completely the same manner as in Example 1 except the use of the zinc oxide powder A4. The results of the same evaluations as in Example 1 are shown in Table 1.

Example 5

Instead of the zinc oxide powder A1, a zinc oxide powder A5 (BET specific surface area: 5.0 m$^2$/g, apparent specific volume measured by loose packing method: 2.0 mL/g, apparent specific volume measured by tapping method: 1.0 mL/g, A1/E2 in Formula (1): 0.10, a in Formula (1): 0.009, (M2−M1)/E2 in Formula (2): 0.078, and crystallite diameter: 37 nm) was prepared. A surface-treated zinc oxide powder B5 of Example 5 and a dispersion C5 containing the surface-treated zinc oxide powder B5 were obtained in completely the same manner as in Example 1 except the use of the zinc oxide powder A5. The results of the same evaluations as in Example 1 are shown in Table 1.

Example 6

Instead of the zinc oxide powder A1, a zinc oxide powder A6 (BET specific surface area: 51.2 m$^2$/g, apparent specific volume measured by loose packing method: 5.5 mL/g, apparent specific volume measured by tapping method: 3.1 mL/g, A1/E2 in Formula (1): 0.20, a in Formula (1): 0.003, (M2−M1)/E2 in Formula (2): 0.084, and crystallite diameter: 15 nm) was prepared. A surface-treated zinc oxide powder B6 of Example 6 and a dispersion C6 containing the surface-treated zinc oxide powder B6 were obtained in completely the same manner as in Example 1 except the use of the zinc oxide powder A6. The results of the same evaluations as in Example 1 are shown in Table 1.

Comparative Example 1

Instead of the zinc oxide powder A1, a zinc oxide powder A7 (BET specific surface area: 34.1 m²/g, apparent specific volume measured by loose packing method: 1.6 mL/g, apparent specific volume measured by tapping method: 1.1 mL/g, A1/E2 in Formula (1): 0.25, a in Formula (1): 0.006, (M2−M1)/E2 in Formula (2): 0.015, and crystallite diameter: 15 nm) was prepared. A surface-treated zinc oxide powder B7 of Comparative Example 1 and a dispersion C7 containing the surface-treated zinc oxide powder B7 were obtained in completely the same manner as in Example 1 except the use of the zinc oxide powder A7. The results of the same evaluations as in Example 1 are shown in Table 1.

Comparative Example 2

Instead of the zinc oxide powder A1, a zinc oxide powder A8 (BET specific surface area: 10.5 m²/g, apparent specific volume measured by loose packing method: 1.6 mL/g, apparent specific volume measured by tapping method: 1.1 mL/g, A1/E2 in Formula (1): 0.23, a in Formula (1): 0.016, (M2−M1)/E2 in Formula (2): 0.014, and crystallite diameter: 25 nm) was prepared. A surface-treated zinc oxide powder B8 of Comparative Example 2 and a dispersion C8 containing the surface-treated zinc oxide powder B8 were obtained in completely the same manner as in Example 1 except the use of the zinc oxide powder A8. The results of the same evaluations as in Example 1 are shown in Table 1.

Comparative Example 3

Instead of the zinc oxide powder A1, a zinc oxide powder A9 (BET specific surface area: 4.5 m²/g, apparent specific volume measured by loose packing method: 1.4 mL/g, apparent specific volume measured by tapping method: 0.8 mL/g, A1/E2 in Formula (1): 0.22, a in Formula (1): 0.036, (M2−M1)/E2 in Formula (2): 0.078, and crystallite diameter: 45 nm) was prepared. A surface-treated zinc oxide powder B9 of Comparative Example 3 and a dispersion C9 containing the surface-treated zinc oxide powder B9 were obtained in completely the same manner as in Example 1 except the use of the zinc oxide powder A9. The results of the same evaluations as in Example 1 are shown in Table 1.

TABLE 1

| | | Example 1 | Example 2 | Example 3 | Example 4 | Example 5 | Example 6 | Comparative Example 1 | Comparative Example 2 | Comparative Example 3 |
|---|---|---|---|---|---|---|---|---|---|---|
| Zinc oxide powder | BET specific surface area (X) (m²/g) | 39.8 | 29.6 | 34.6 | 36.5 | 5.0 | 51.2 | 34.1 | 10.5 | 4.5 |
| | Loosely packed volume (mL/g) | 5.2 | 5.1 | 6.4 | 3.7 | 2.0 | 5.5 | 1.6 | 1.6 | 1.4 |
| | Tapped volume (mL/g) | 2.9 | 2.7 | 2.9 | 2.2 | 1.0 | 3.1 | 1.1 | 1.1 | 0.8 |
| | Loosely packed volume/tapped volume | 1.8 | 1.9 | 2.2 | 1.6 | 2.0 | 1.8 | 1.5 | 1.5 | 1.6 |
| | A1 | 1026 | 583 | 590 | 3825 | 5383 | 1121 | 2602 | 7436 | 13579 |
| | E2 | 6220 | 3557 | 4880 | 5317 | 52519 | 5578 | 10422 | 32318 | 61730 |
| | M1 | 1366 | 805 | 1365 | 1788 | 7256 | 1158 | 1590 | 5569 | 8442 |
| | M2 | 1871 | 1144 | 1820 | 1921 | 11371 | 1625 | 1715 | 6022 | 13259 |
| | A1/E2 | 0.16 | 0.16 | 0.12 | 0.72 | 0.10 | 0.20 | 0.25 | 0.23 | 0.22 |
| | Proportional constant a | 0.003 | 0.004 | 0.002 | 0.018 | 0.008 | 0.003 | 0.006 | 0.016 | 0.036 |
| | Formula (1)* | O | O | O | O | O | O | O | O | X |
| | Crystallite diameter (nm) | 16 | 21 | 18 | 16 | 37 | 15 | 15 | 25 | 45 |
| | BET-converted diameter (nm) | 26.9 | 36.2 | 30.9 | 29.3 | 214.1 | 20.9 | 31.4 | 101.9 | 237.8 |
| | Crystallite diameter/BET-converted diameter | 0.59 | 0.58 | 0.58 | 0.55 | 0.17 | 0.72 | 0.48 | 0.25 | 0.19 |
| | Amount of transition metals | O | O | O | O | O | O | X | X | O |
| | Before cracking L* | 93.3 | 93.2 | 92.5 | 92.8 | 93.5 | 93.3 | 92.0 | 92.6 | 93.2 |
| | a* | −1.0 | −1.1 | −0.2 | −3.8 | −1.1 | −1.1 | −4.4 | −2.7 | −1.6 |
| | b* | 3.8 | 3.4 | 3.6 | 5.4 | 3.0 | 4.2 | 10.3 | 7.3 | 5.5 |
| | W* | 92.2 | 92.3 | 91.7 | 90.2 | 92.7 | 92.0 | 86.3 | 89.3 | 91.1 |
| | After cracking L* | 92.7 | 92.8 | 92.2 | 92.5 | 93.1 | 92.9 | 91.6 | 92.1 | 92.7 |
| | a* | −1.0 | −1.2 | −0.1 | −4.0 | −1.2 | −1.1 | −4.5 | −2.9 | −1.8 |
| | b* | 4.1 | 3.7 | 3.7 | 5.8 | 3.5 | 4.6 | 11.6 | 9.0 | 7.2 |
| | W* | 91.6 | 91.8 | 91.4 | 89.7 | 92.2 | 91.5 | 85.0 | 87.7 | 89.6 |
| | ΔW* | 0.6 | 0.5 | 0.3 | 0.5 | 0.6 | 0.5 | 1.3 | 1.6 | 1.5 |
| Dispersion | Initial viscosity (mPa · s) | 90 | 80 | 60 | 60 | 20 | 110 | 50 | 30 | 23 |
| | Viscosity after 28 days at 50° C. (mPa · s) | 160 | 120 | 100 | 90 | 40 | 180 | 80 | 50 | 48 |
| | Transmittance at 308 nm (%) | 33 | 38 | 32 | 30 | 45 | 30 | 27 | 42 | 44 |
| | Transmittance at 555 nm (%) | 88 | 84 | 90 | 90 | 65 | 90 | 92 | 75 | 62 |

*Regarding Formula (1), "O" is indicated when Formula (1) is satisfied, and 'X" is indicated when not satisfied.
**Regarding Formula (2), "O" is indicated when Formula (2) is satisfied, and 'X" is indicated when not satisfied.

In Table 1, the loosely packed volume represents the apparent specific volume measured by the loose packing method. The tapped volume represents the apparent specific volume measured by tapping method.

It was confirmed from the comparison between Example 1 to Example 6 and Comparative Example 1 to Comparative Example 3 that, in the zinc oxide powder in which the BET specific surface area was 1.5 m²/g or more and 65 m²/g or less, the value obtained from the formula: the apparent specific volume (mL/g) measured by the loose packing method/the apparent specific volume (mL/g) measured by the tapping method was 1.5 or more and 2.5 or less, and Formula (1) and Formula (2) were satisfied, even when high energy was applied thereto, ΔW* was 1 or less, and the coloration of the zinc oxide powder was suppressed.

INDUSTRIAL APPLICABILITY

Even when the zinc oxide powder of the present invention is dispersed with a high energy, coloration of the zinc oxide powder is suppressed. Therefore, the zinc oxide powder of the present invention is excellent in terms of stability in the case of being applied to dispersions, paints, and cosmetics and has a significant industrial value.

The present invention is capable of providing a zinc oxide powder coloration of which is suppressed even when a high energy is applied thereto, a dispersion, a paint, and a cosmetic that each contain the zinc oxide powder.

What is claimed is:

1. A zinc oxide powder,
wherein a BET specific surface area (X) of the powder is 1.5 m²/g or more and 65 m²/g or less,
a value obtained by a formula: an apparent specific volume (mL/g) measured by a loose packing method of the zinc oxide powder/an apparent specific volume (mL/g) measured by a tapping method of the zinc oxide powder is 1.5 or more and 2.5 or less,
and
Formula (1) and Formula (2) shown below are satisfied:

$$A1/E2 = aX + 0.06 \quad (1)$$

$$(M2 - M1)/E2 \geq 0.02 \quad (2)$$

(X represents a BET specific surface area (unit: m²/g) of the zinc oxide powder; A1 represents a spectrum value of a peak present in the vicinity of 580 cm⁻¹ in a Raman spectrum of the zinc oxide powder which is obtained by Raman spectroscopy; E2 represents a spectrum value of a peak present in the vicinity of 437 cm⁻¹ in the Raman spectrum; a represents a value of 0.001 or more and 0.025 or less; M2 represents a maximum value of a spectrum within a range of 1091 cm⁻¹ to 1170 cm⁻¹ of the Raman spectrum; and M1 represents a maximum value of a spectrum within a range of 1020 cm⁻¹ to 1090 cm⁻¹ of the Raman spectrum).

2. The zinc oxide powder according to claim 1, wherein the apparent specific volume (mL/g) measured by the loose packing method is 1.0 mL/g or more and 7.5 mL/g or less.

3. The zinc oxide powder according to claim 1, wherein a total amount of metals, which are selected from the group consisting of vanadium, chromium, manganese, iron, cobalt, nickel, and copper and are contained in the zinc oxide powder, is 0.5 ppm or more and 20 ppm or less.

4. The zinc oxide powder according to claim 3, wherein a crystallite diameter of the powder is 15 nm or more and 60 nm or less.

5. The zinc oxide powder according to claim 4, wherein, when L*, a*, b* of the zinc oxide powder are measured with a spectroscopic color difference meter, regarding W* that is obtained with Formula (3) shown below, a difference of the W* before and after cracking the zinc oxide powder until D98 of the zinc oxide powder reaches 500 μm or less is 0.1 to 1.2, $$W^* = 100 - ((100 - L^*)^2 + (a^*)^2 + (b^*)^2)^{1/2} \quad (3).$$

6. The zinc oxide powder according to claim 1, wherein the zinc oxide powder is a surface-treated powder which is surface-treated with at least one of an inorganic component and an organic component.

7. A dispersion comprising:
the zinc oxide powder according to claim 1; and
a dispersion medium.

8. A paint comprising:
the zinc oxide powder according to claim 1;
a resin; and
a dispersion medium.

9. A cosmetic comprising:
the zinc oxide powder according to claim 1; and
a dispersion medium.

10. The zinc oxide powder according to claim 1, wherein the apparent specific volume (mL/g) measured by the loose packing method is a value which is measured in accordance with JIS K5101-12-1, and
the apparent specific volume (mL/g) measured by the tapping method is a value measured by
passing a zinc oxide powder through a sieve having a mesh diameter of 500 μm,
adding the zinc oxide powder which has been passed through the sieve to a 150 mL graduated cylinder, wherein the weight of the cylinder is known, until the volume of the powder becomes 100 mL,
measuring the weight of the graduated cylinder which includes the powder,
covering the measured graduated cylinder with a lid,
fixing the covered graduated cylinder to a bulk density-measuring device, and performing tapping thereon 50 times,
reading the volume of the zinc oxide powder after tapping, and
obtaining a value as the apparent specific volume by dividing the volume of the zinc oxide powder after tapping by the weight of the zinc oxide powder in the graduated cylinder.

* * * * *